(12) United States Patent
Kilpatrick et al.

(10) Patent No.: US 6,716,178 B1
(45) Date of Patent: Apr. 6, 2004

(54) APPARATUS AND METHOD FOR PERFORMING THERMAL AND LASER DOPPLER VELOCIMETRY MEASUREMENTS

(75) Inventors: Deborah Kilpatrick, Mountain View, CA (US); Jeffrey T. Ellis, Mountain View, CA (US); Bridget A. Hurley, Mountain View, CA (US); Jeong S. Lee, Diamond Bar, CA (US); Robert D. Ainsworth, Scotts Valley, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 72 days.

(21) Appl. No.: 09/872,299

(22) Filed: May 31, 2001

(51) Int. Cl.⁷ ............................................... A61B 10/00
(52) U.S. Cl. ........................................ 600/504; 600/342
(58) Field of Search .................... 600/504, 505, 600/310, 342–343, 478; 356/28.5; 374/121; 604/523

(56) References Cited

U.S. PATENT DOCUMENTS

| | | |
|---|---|---|
| 4,587,972 A | 5/1986 | Morantte, Jr. |
| 4,671,288 A | 6/1987 | Gough |
| 4,794,931 A | 1/1989 | Yock |
| 4,887,605 A | 12/1989 | Angelsen et al. |
| 4,920,967 A | 5/1990 | Cottonaro et al. |
| 4,926,875 A | 5/1990 | Rabinovitz et al. |
| 5,022,399 A | 6/1991 | Biegeleisen |
| 5,047,213 A | 9/1991 | Finlan et al. |
| 5,167,233 A | 12/1992 | Eberle et al. |
| 5,284,146 A | 2/1994 | Czar et al. |
| 5,325,860 A | 7/1994 | Seward et al. |
| RE34,695 E | 8/1994 | Mar et al. |
| 5,345,940 A | 9/1994 | Seward et al. |
| 5,411,476 A | 5/1995 | Abrams et al. |
| 5,571,086 A | 11/1996 | Kaplan et al. |
| 5,582,171 A | 12/1996 | Chornenky et al. |
| 5,603,820 A | 2/1997 | Malinski et al. |
| 5,744,902 A | 4/1998 | Vig |
| 5,756,351 A | 5/1998 | Isacoff et al. |
| 5,782,760 A | 7/1998 | Schaer |
| 5,855,563 A | 1/1999 | Kaplan et al. |
| 5,873,835 A | 2/1999 | Hastings et al. |
| 5,876,121 A * | 3/1999 | Burns et al. ................. 374/161 |
| 5,876,345 A | 3/1999 | Eaton et al. |
| 5,902,308 A | 5/1999 | Murphy |
| 5,919,129 A | 7/1999 | Vandre |
| 5,935,075 A | 8/1999 | Casscells et al. |
| 5,951,471 A | 9/1999 | de la Rama et al. |
| 5,951,482 A | 9/1999 | Winston et al. |
| 5,957,903 A | 9/1999 | Mirzaee et al. |
| 5,980,471 A | 11/1999 | Jafari |
| 5,984,909 A | 11/1999 | Lurie et al. |
| 6,001,085 A | 12/1999 | Lurie et al. |
| 6,023,638 A | 2/2000 | Swanson |
| 6,141,576 A | 10/2000 | Littmann et al. |
| 2001/0035503 A1 * | 11/2001 | Quistorff et al. .......... 250/495.1 |
| 2002/0026127 A1 * | 2/2002 | Balbierz et al. ............ 600/567 |
| 2002/0159499 A1 * | 10/2002 | Ruffa ......................... 374/161 |

OTHER PUBLICATIONS

Sano, O. et al, "Simultaneous Measurements of Velocity and Temperature by the Use of a Laser Doppler Velocimeter," Phys. of Fluids, V. 28, No. 3, pp. 818–822, Mar. 1985.*

(List continued on next page.)

Primary Examiner—John A. Jeffery
(74) Attorney, Agent, or Firm—Blakely, Sokoloff, Taylor & Zafman LLP

(57) ABSTRACT

A therapeutic intravascular device and method for performing thermal and laser Doppler velocimetry measurements. In one embodiment, the therapeutic intravascular device includes an elongated member having first and second optical fibers longitudinally disposed therethrough, the first optical fiber for performing a laser Doppler velocity measurement of a fluid within a body lumen, the second optical fiber for performing a temperature measurement within the body lumen.

27 Claims, 7 Drawing Sheets

OTHER PUBLICATIONS

Young, S. R. et al, "The Effect of Therapeutic Ultrasound on Angiongenesis," Ultrasound in Med. & Biol., vol. 16, No. 3, pp. 261–269, 1990.*

Beekhuizen H, van Furth R. "Monocyte Adherence to Human Vascular Endothelium." *Journal of Leukocyte Biology* 1993, vol. 54, 363–378.

Casscells W, Hathorn B, David M, Krabach T, Vaugh W, McAllister H, et al., "Thermal detection of Cellular Infiltrates in Living Atherosclerotic Plaques: Possible Implications for Plaque Rupture and Thrombosis." *Lancet* 1996, vol. 347, 1447–1451.

Einav S. "Laser Doppler Fiberscope Anemometer for In Vivo Blood Flow Measurements." *Optical Fibers in Medicine VIII* 1993, 62–73.

Hangiandreou N, Toggart E, Mistretta C. "Investigation of the Performance of Two Types of the Doppler Catheter in Vitro." *Catherization and Cardiovascular Diagnosis* 1989, vol. 18, 108–117.

Ikeda U, Takahashi M, Shimada K. "Monocyte–Endothelial Cell Interaction in Atherogenesis and Thrombosis." *Clinical Cardiology* 1997, vol. 21, 11–14.

Kern M, de Bruyne B, Pijls N. "From Research to Clinical Practice: Current Role of Intracoronary Physiologically Based Decision making in the Cardiac Catherterization Laboratory." *Journal of the American College of Cardiology* 1997, vol. 30, 613–620.

Kilpatrick D, Kajiya F, Ogasawara Y. "Fiber Optic Laser Doppler Measurement of Intravascular Velocity." *Australasian Physical and Engineering Sciences in Medicine* 1998, vol. 11, 5–14.

Nishhara H, Koyama J, Hoki N, Kajiya F, Hironaga M, Kano M. "optical–Fiber Laser Doppler Velocimeter for High–Resolution Measurement of Pulsatile Blood Flows." *Applied Optics* 1982, vol. 21, 1785–1790.

Serruys P, di Mario C, Piek J, Shcroeder E, Vrints C, Probst P, de Bruyne B, et al., "Prognostic Value of Intracoronary Flow Velocity and Diameter Stenosis in Assessing the Short—and Long–Term Outcomes of Coronary Balloon Angioplasty: *The Debate Study*." *Circulation* 1997, vol. 96, 3369–3377.

Stefandadis C, Diamantopoulos L, Vlachopoulos C, Tsiamis E, Dernellis J, Toutouzas K, et al. "Thermal Heterogeneity Within Human Atherosclerotic Coronary Arteries Detected In Vive: A New Method of Detection by Application of a Special Thermography Catheter." *Circulation* 1999, vol. 99, 1965–71.

Doucette J., Corl D., Payne H., Flynn A., Goto M., Nassi M., Segal J. "Validation of a Doppler Guidewire for Intravascular Measurement of Coronary Artery Flow Velocity", Circulation 1992, vol. 85, 382–385.

Dib N., Bajwa T., Shalev Y., Nesto R. Schmidt D., "Validation of Doppler FloWire for Measurement of Coronary Flow Reserve in Humans". *Catheterization and Cardiovascular Diagnosis* 1998, vol. 45, 382–385.

Pijls N., Van Gelder B., Van der Voort P., Peels K., Bracke F., Bonnier H., El Gamal M., "Fractional Flow Reserve: A Useful Index to Evaluate the Influence of an Epicardial Coronary Stenosis on Myocardial Blood Flow." *Circulation* 1995, vol. 92, 3183–3193.

Bridget Hurley's Lab Book 5449, pp. 28–29.

Jeff Ellis Lab Book 5528, pp. 103–107.

Davis R., "Bursting The Deadly Danger Of Aortic Aneurysms", USA Today Mar. 16, 2000, Section 10D.

Krohn D., "Two Ways of Sensing with Fibers for Two Kinds of Applications", 1998 *The Photonics Design and Applications Handbook*, Sensors, H–203.

Engineering & Marketing Staff, "An Introduction to Fiber Optics", *1998 The Photonics Design and Applications Handbook*, Fiber Optics, H–176.

Bhatia V., Murphy K., de Vires M., Sen M., D'Alberto T.,"A Comparative Evaluation of the Types and Applications of Various Sensors" 1998, *The Photonics Design and Applications Handbook*, Sensors, H–199.

McCann B., "Three Silica–Core Fibers Rise to Top in Medical Laser Uses", 1998, *The Photonics Design and Applications Handbook*, Fibers/Medical Lasers, H–209.

McCann B., "Fiber Holds the Key to Medical Lasers' Success", May 1990, *Photonics Spectra*, p. 127.

Moslem A., "Transmission properties of optical fibers at two laser wavelengths: 660 nm & 2100 nm", PTICAL Materials, Aug. 19, 1991, Center for Laser Research, Oklahoma State University, p. 27–41.

* cited by examiner

APPARATUS AND METHOD FOR PERFORMING THERMAL AND LASER DOPPLER VELOCIMETRY MEASUREMENTS

BACKGROUND OF THE INVENTION

1. Field of the Invention

This invention relates to the field of medical diagnosis and treatment by means of a device having Doppler velocimetry and thermal sensing capability. More specifically, the present invention relates to a therapeutic medical device for performing thermal measurements and laser Doppler velocimetry measurements within a body lumen.

2. Description of Related Art

Arteriosclerosis, or more specifically atherosclerosis, is a common human ailment arising from the deposition of fatty-like substances, referred to as atheroma or plaque, on the walls of systemic, peripheral, and coronary blood vessels. When deposits accumulate in localized regions of a vessel, blood flow can be occluded or restricted, increasing the risk of heart attack or stroke.

Numerous approaches for reducing and removing such vascular deposits have been proposed, including balloon angioplasty, where a balloon-tipped catheter is used to dilate a region of atheroma; atherectomy, where a blade or other cutting element is used to sever and remove the atheroma; laser angioplasty, where laser energy is used to ablate (i.e., remove) at least a portion of the atheroma; or stenting, where a stent is deployed (permanently or temporarily) at the site of vascular deposits (sometimes following balloon angioplasty). The vast majority of these therapeutic devices, however, are being used with very little information about the in vivo biological environment, including for example, the information on physiology, hemorheology, vascular biology or histology and histochemistry of the vasculature being treated. Without such information available to the physician, "lesion specific" treatment, as well as preventive measures, cannot be adequately envisioned or planned.

Evidence reported in the medical field suggests that thermal heterogeneity in the atherosclerotic plaque may reflect its propensity to be vulnerable to rupture. Both in vitro and in vivo data on human and animal lesions have indicated that thermal gradients in the tissue are related to the presence of inflammatory macrophages, and the most recent data have correlated thermal profiles with clinical presentation in humans. There is, therefore, scientific support that inflammation can be reflected in local thermal gradients in vascular tissue in vivo. Of particular interest is the application of thermal sensing to assess the risk of thrombotic complications post-intervention. An acute inflammatory response, such as that induced by endovascular percutaneous transluminal coronary angioplasty (PTCA) and/or stenting, may induce circulating monocyte binding and migration across the endothelium of the vessel wall to gain access to the injury site.

Studies have suggested that physiologic, and more specifically flow-based, components of the lesion environment can yield insight into lesion assessment and management. A variety of flow-based indices, most notably the coronary flow reserve (CFR), can be used to elucidate clinically relevant relations of physiologic lesion environment and the functional status of the treatment. A recent medical clinical trial concluded that based on target criteria established for residual percent diameter stenosis and final CFR, the percentage of acute procedural success observed in the trials could be increased up to 50 percent if some type of flow-based Doppler guidance were used.

Current generation medical devices force cardiovascular treatment procedures to employ one device for the diagnostic phase of the procedure and a second device for the treatment phase of the procedure. Given the tendency within the medical community to move toward shorter procedural times, spot PTCA, and even direct and/or spot stenting in many cases, the use of an additional device required to obtain diagnostic-type information is not generally an acceptable alternative.

Previous attempts to make a combined diagnostic/treatment biomedical device (such as a guidewire-based platform or a catheter-based system) with the capability of directly measuring flow-based variables have yielded devices either too bulky or too cumbersome to use during intravascular or intraluminal procedures. Current generation biomedical devices that have attempted to combine diagnostic and therapeutic capabilities consist mainly of ultrasound Doppler guidewires and ultrasound Doppler catheters.

Ultrasound Doppler guidewires have a number of disadvantages and limitations. One disadvantage is that the ultrasound Doppler guidewire measurement system creates a comparatively large sample volume (about 1 $mm^3$). Another disadvantage associated with ultrasound Doppler guidewire devices is the susceptibility to signal loss very close to the lesion site. Furthermore, ultrasound Doppler guidewires require extensive operator input to optimize the signal quality in regions of disturbed flow.

Ultrasound Doppler catheter systems have disadvantages and limitations similar to those of ultrasound Doppler guidewire devices. The catheter-based ultrasound Doppler measurement system creates a comparatively large sample volume (about 1 $mm^3$). Another disadvantage of current generation ultrasound Doppler catheter systems is the reduced catheter body flexibility due to the multiple junctions required in the design of these catheters. Another limitation of current ultrasound Doppler catheter designs is that because the ultrasonic crystals are mounted on either the side or end of the catheter body, instability of the catheter tip position can result, making it difficult to localize the measurement site.

Furthermore, most current ultrasound Doppler catheter and guidewire designs lack the means of having combined therapeutic/diagnostic capability, especially for intravascular or coronary applications. The result is that therapeutic strategies are often unilaterally rendered without relevant information concerning the lesion, surrounding vasculature, or the biomechanical environment—information which, if available, could be appropriately used to improve both acute and chronic outcomes for the patient.

The disadvantages of current generation ultrasound Doppler catheters and guidewires can be overcome in the present invention by incorporating thermal sensing and laser Doppler velocimetry (LDV) technologies onto a therapeutic catheter or therapeutic guidewire assembly. Laser Doppler velocimetry is a technique for measuring the speed of small particles. Generally, for LDV measurements, small particles suspended in a fluid are illuminated by a laser beam and the light scattered to various angles is compared to light in a reference beam to determine the Doppler shift of the scattered light. The Doppler shift of the light depends on the speed of the particles and the angle of measurement.

SUMMARY OF THE INVENTION

A therapeutic medical device for performing thermal and laser Doppler velocimetry measurements and method of using the same are described. In one embodiment, the therapeutic medical device includes an elongated member having at least first and second optical fibers longitudinally disposed therethrough, the first optical fiber to perform a laser Doppler velocity measurement of a fluid within a body lumen, the second optical fiber to perform a temperature measurement within the body lumen. Incorporating LDV technology and thermal sensing capability into a therapeutic medical device such as a catheter or a guidewire system provides diagnostic information of the physiologic environment of the lesion before, during, or after a therapeutic procedure.

BRIEF DESCRIPTION OF THE DRAWINGS

The present invention is illustrated by way of example and not limitation in the accompanying figures.

DETAILED DESCRIPTION OF THE INVENTION

Embodiments of apparatuses and methods to perform therapeutic treatment and diagnosis of a patient's vasculature through the use of an intravascular device having thermal and laser Doppler velocimetry (LDV) measurement capabilities are described.

In the following detailed description, numerous specific details are set forth in order to provide a more thorough understanding of the present invention. However, it will be apparent to those skilled in the art to which this invention pertains that the present invention is not limited in scope by these specific details. In other instances, well-known devices, methods, procedures, and individual components have not been described in detail so as not to obscure aspects of the present invention.

Although the present invention is described generally in terms of its use within the vascular system of a patient, it should be noted that the apparatus and method of the present invention may also be advantageously employed in other body lumens, organs and structures, such as the esophagus, the stomach, the colon, the uterus, saphenous vein grafts, heart valves, and other body cavities, lumens, channels, and canals.

Figure 1A:
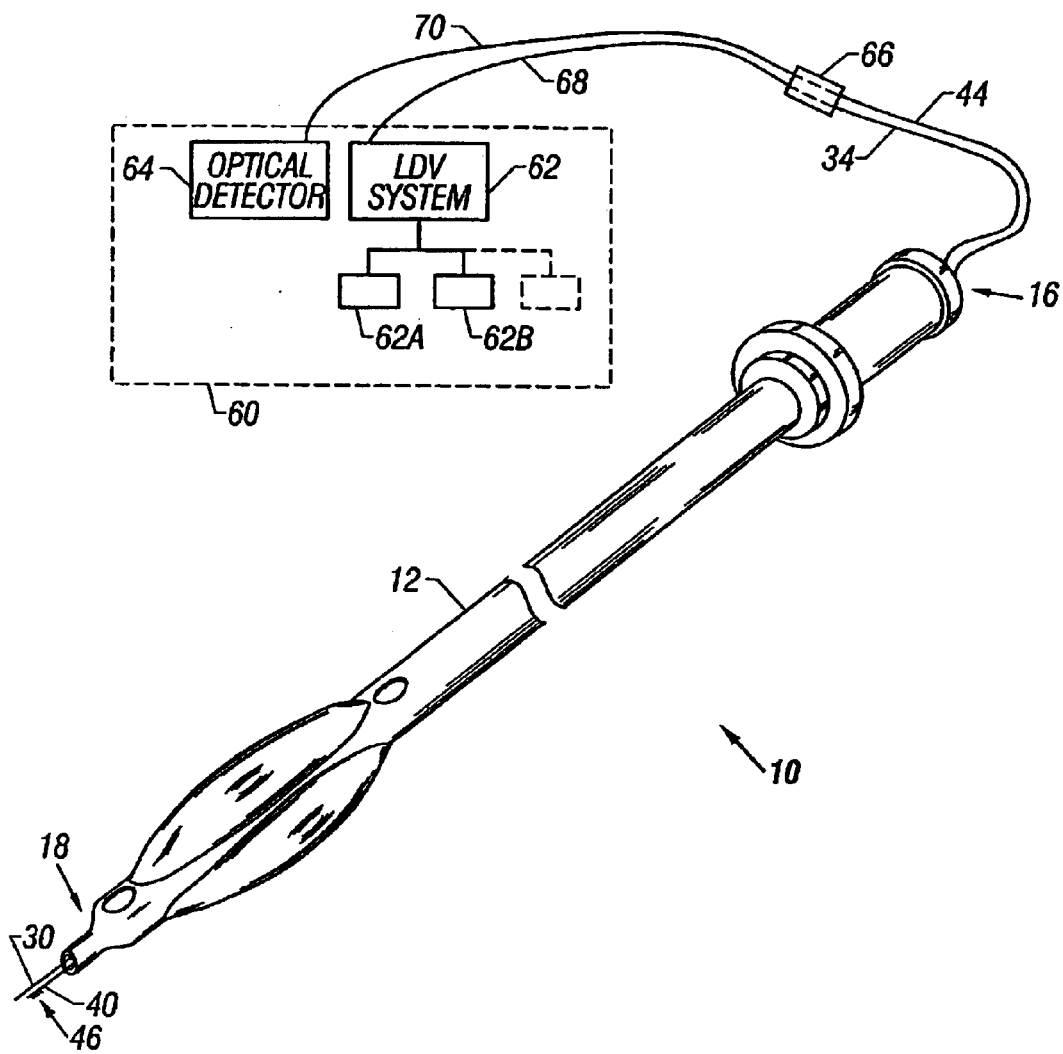
FIG. 1A is a perspective view illustrating generally an embodiment of a therapeutic medical device for performing thermal and laser Doppler velocimetry measurements coupled to an LDV/thermal sensing apparatus and data processing system.
Figures 1B, 1C:
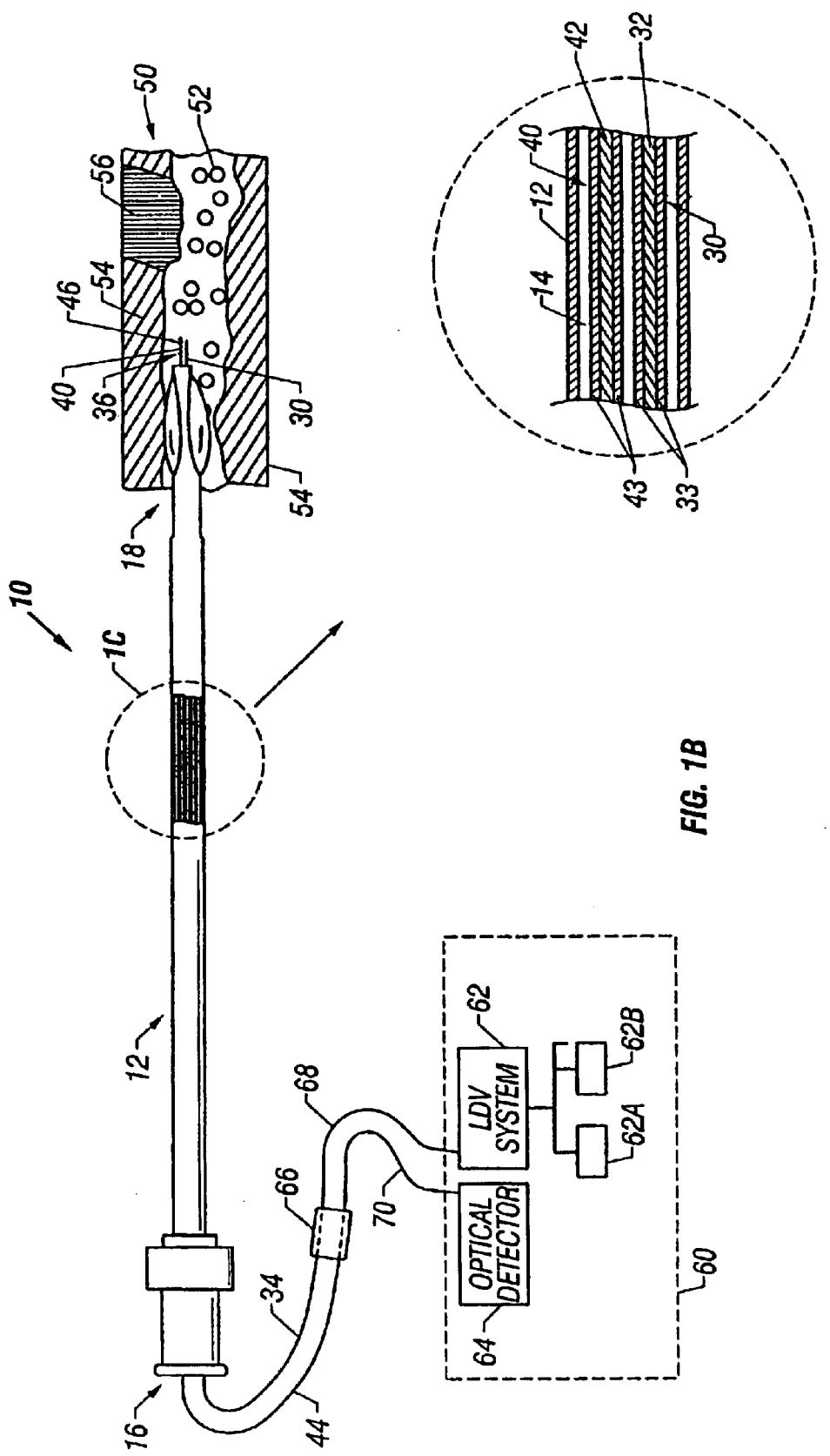
FIG. 1B is a schematic side view partial section of therapeutic medical device of FIG. 1A.
FIG. 1C is a schematic partial section side view of the elongated member of therapeutic medical device of FIG. 1B showing at least two optical fibers positioned therethrough.

FIGS. 1A–1C illustrate generally an exemplary embodiment of a therapeutic intravascular device 10 for performing thermal and laser Doppler velocimetry measurements coupled to an LDV/thermal sensing apparatus and data processing system 60. FIG. 1A is a perspective view of therapeutic intravascular device 10. In FIG. 1B, the therapeutic intravascular device 10 is schematically shown to be inserted into a body lumen 50 of a patient. The intravascular device 10 may include any medical device, such as a catheter or a guidewire operatively coupled to catheter, used to treat intravascular conditions.

With reference to FIGS. 1A–1C, the therapeutic medical device, such as intravascular device 10 generally includes an elongated member 12 having at least one lumen 14 (shown in partial section side view of FIG. 1C) extending longitudinally therethrough. The therapeutic intravascular device 10 further includes at least first and second optical fibers 30, 40 extending longitudinally through lumen 14, the first optical fiber 30 to perform a laser Doppler velocity measurement of a fluid 52 within the body lumen 50 and the second optical fiber 40 to perform a temperature measurement within the body lumen 50. It will be noted that it is within the scope of the present invention to have the intravascular device 10 incorporate multiple optical fibers or a fiber optic bundle for each of the first and second optical fibers 30, 40. This arrangement may be advantageous for applications that would require performing thermal measurements and/or LDV measurements simultaneously at multiple sites in a vessel.

As shown in the side view partial section enlargement of FIG. 1C, generally, first and second optical fibers 30, 40 may include a thin filament of drawn or extruded glass or plastic/polymer having a central core 32, 42 and a cladding 33, 43 of lower index material to promote internal reflection of light. The central core 32, 42 is the light-transmitting portion of the optical fibers 30, 40.

Continuing with reference to FIGS. 1A–1C, in an embodiment, the first optical fiber 30 is a single strand, single-mode glass optical fiber generally disposed within lumen 14 of the elongated member 12. First optical fiber 30 may be fixedly coupled to at least one point within the elongated member 12 or alternatively, it may be movable, e.g. slideable, within the elongated member lumen 14. First optical fiber 30 typically extends slightly beyond both the proximal and distal ends 16, 18 of elongated member 12. A proximal extension length 34 of first optical fiber 30 allows for connection of the first optical fiber 30 to an LDV system 62 through a mechanical coupler 66 and an LDV optical fiber 68. A distal extension length of first optical fiber 30 allows for any necessary steps required to make the first optical fiber tip 36 flush with, or extend slightly beyond the distal end 18 of the elongated member 12. Such steps can include, but are not limited to, cleaving the first optical fiber 30 at an angle, cutting the fiber 30 with a perpendicular face, or removing the fiber cladding as necessary to optimize light transmission/reception.

First optical fiber 30 may be manufactured of glass or plastic and may have an outer diameter in a range of approximately 100–250 microns ($\mu$m) (0.004–0.01 inches). As an example, first optical fiber 30 may have an outer diameter of about 155 $\mu$m (0.006 inches) with a core 32 diameter of about 9.3 $\mu$m (0.000372 inches). The LDV optical fiber 68 may also be manufactured of glass or plastic and may have an outer diameter of about 200–350 $\mu$m (0.008–0.014 inches). In an example embodiment, LDV optical fiber 68 may have an outer diameter of about 250 $\mu$m (0.01 inches) with a core diameter of about 9.3 $\mu$m (0.000372 inches). It will be noted that selection of optical fibers 30, 68 is not limited to only the example arrangements and diameters discussed above. Other more flexible optical fibers, such as those with polymer-based claddings, as well as optical fibers having smaller diameters may be used in practicing this invention.

Continuing with reference to embodiment shown in FIGS. 1A–1C, the second optical fiber 40 generally includes a single strand, single-mode glass optical fiber also disposed within lumen 14 of elongated member 12. Second optical fiber 40 may be fixedly coupled to at least one point within the elongated member 12 or alternatively, it may be movable, e.g. slideable, within elongated member 12. Second optical fiber 40 typically extends beyond both the proximal and distal ends 16, 18 of elongated member 12. A proximal extension length 44 of second optical fiber 40 allows for connection of the second optical fiber 40 to an optical detector 64 through the common mechanical coupler 66 and a connecting optical fiber 70 or through a separate mechanical coupler (not shown) and the connecting optical fiber 70. A portion of distal extension length of second optical fiber 40 has a Bragg diffraction grating 46 formed thereon which, when exposed to light from a light source, is used for performing a temperature measurement of a fluid 52, e.g. blood, within a body lumen 50, as well as of other physical structures, such as the arterial wall 54, restenosed area 56, etc. of the body lumen 50.

Second optical fiber 40 may be manufactured of glass or plastic and may have an outer diameter of about 200–350 $\mu$m (0.008–0.014 inches). In an example embodiment, second optical fiber 40 may have an outer diameter of about 250 $\mu$m (0.01 inches) with a core diameter of about 9.3 $\mu$m (0.000372 inches). Connecting optical fiber 70 is generally manufactured of the same materials, e.g. glass, and may have a physical configuration similar to that of second optical fiber 40 but without having a Bragg diffraction grating thereon. Connecting optical fiber 70 may have an outer diameter in a range of approximately 200–350 $\mu$m (0.008–0.014 inches). It will be noted that selection of optical fibers 40, 70 is not limited to only the example arrangements and diameters discussed above. Other more flexible optical fibers, such as those with polymer-based claddings, as well as optical fibers having smaller diameters may be used in practicing this invention.

During its use in a medical procedure, the first fiber optic 30 of the therapeutic medical device 10 transmits and receives light for determining fluid flow velocities through a laser Doppler velocimetry technique, while the second optical fiber 40, with its Bragg diffraction grating 46 written into it, measures local temperature.

Laser Doppler velocimetry is a non-intrusive method for measuring flow velocities. The LDV method is a light-based technique that focuses a small sample volume, often on the order of $10^{-4}$ mm$^3$, very near the tip of the intravascular device 10 for detailed interrogation of a flow space near the tip of the therapeutic intravascular device 10. Generally, to perform LDV measurements, light is transmitted from a laser source 62A in the LDV system 62 through the optical fibers 30, 34, 68 and is scattered off of formed blood elements 52. The scattered light is collected by a detector 62B in the LDV system 62 as the light travels back through the optical fibers 30, 34, 68. The frequency content of the scattered light is indicative of the fluid velocity at the measurement site.

In an alternative embodiment, the LDV technology 62 uses intersecting two or more beams from a light source 62A, for example a laser source, and advanced optical data collection and processing equipment 62B to measure motion of individual minute particles as they pass through an imposed fringe pattern. The crossing of laser beams creates a "measurement volume" which consists of an interference fringe pattern of planar layers of high and low intensity light. Minute particles (e.g., 1 $\mu$m to 10 $\mu$m) present in the fluid backscatter the laser light with a frequency proportional to the flow velocity when passing through the measurement volume. The backscattered light is typically converted to an electrical signal with a photodetector or similar device. By using Fast Fourier Transform (FFT) techniques, the Doppler frequency is determined. The flow velocity is calculated with the known distance between the interference fringes and the measured frequency.

Measurements of local fluid temperature are obtained using optical fiber 40 having a Bragg diffraction grating 46 on its distal end. During manufacturing, strain-sensitive grating 46 is inscribed into the core of the optical fiber 40. As grating 46 of the fiber optic undergoes a temperature change due to the fluid temperature conducted along the fiber 40, the fringe spacing will correspondingly expand or contract as the fiber 40 is heated or cooled. The process results in a change in the index of refraction. As a result of this thermal induced strain in the grating, the light through the fiber 40 experiences this change in index of refraction, resulting in a change in the amount of light that is transmitted through the optical fiber 40. The therapeutic intravascular device 10 of this invention may be used to perform temperature measurements of the local fluid, e.g. blood 52, as well as of any body lumen structures, such as the arterial wall 54, etc.

Catheter for Performing LDV and Thermal Measurements

Figure 2:
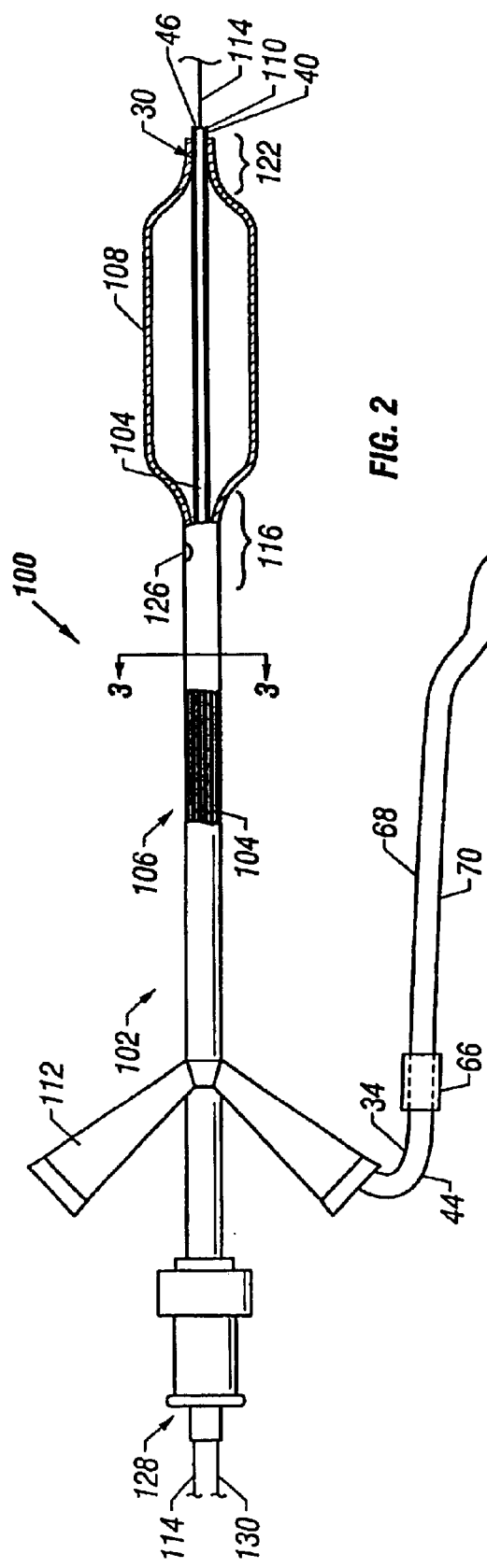
FIG. 2 is a side view partial section of an embodiment of a catheter for performing LDV/thermal sensing measurements coupled to an LDV/thermal sensing apparatus and data processing system.
Figure 2:
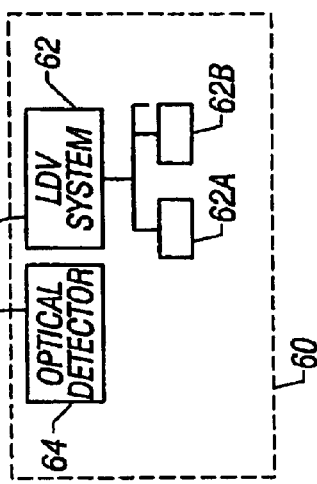

FIGS. 2, 3A–3C schematically illustrate various embodiments of a catheter 100 representing features of this invention. Catheter 100 is an over the wire (OTW) type balloon catheter configured to perform a therapeutic treatment and includes at least first and second optical fibers 30, 40 for performing LDV and thermal measurements. FIG. 2 is a schematic side view representation of the OTW catheter 100.

Figure 3C:
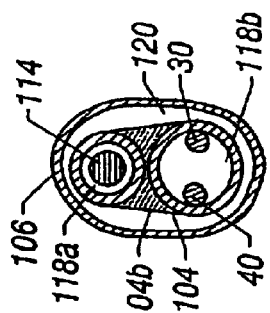
FIG. 3C is a cross-sectional view of another embodiment of catheter of FIG. 2 having a multi-lumen inner member and at least two optical fibers positioned within a lumen of the catheter shaft inner member.
Figure 3B:
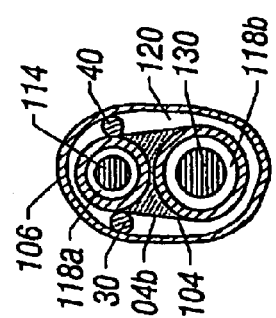
FIG. 3B is a cross-sectional view of an alternate embodiment of catheter of FIG. 2 having a multi-lumen inner member and at least two optical fibers positioned within an intraluminal space of the catheter shaft outer member.
Figure 3A:
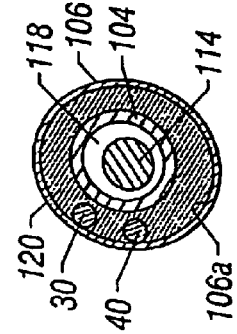
FIG. 3A is a cross-sectional view of the catheter of FIG. 2 having a single lumen inner member and having at least two optical fibers positioned within an intraluminal space of the catheter shaft outer member.

First optical fiber 30 is for performing a laser Doppler velocity measurement of a fluid within the body lumen while the second optical fiber 40 is for performing a temperature measurement within the body lumen. When disposed within the balloon catheter 100, first and second optical fibers 30, 40 may be positioned in a number of configurations, for example within an intraluminal gap or lumen between the catheter shaft inner and outer members, or within a lumen of the inner member. First and second optical fibers 30, 40 may be fixedly coupled to the balloon catheter 100 at one or more points thereof. Alternatively, first and second optical fibers 30, 40 may be movable, e.g. slideable within the balloon catheter 100. These fiber optic/catheter configurations are discussed in detail below. FIG. 3A illustrates a cross-sectional area of the OTW catheter 100 of FIG. 2 having an inner member with a single lumen configuration and an optical fiber disposed within an intraluminal gap formed between the inner and outer members. FIG. 3B illustrates a cross-sectional area of another embodiment of OTW catheter 100 of FIG. 2 having an inner member with a multi-lumen configuration and an optical fiber disposed within an intraluminal gap formed between the inner and outer members. FIG. 3C illustrates a cross-sectional area of an alternative embodiment of OTW catheter 100 of FIG. 2 having an inner member with a multi-lumen configuration and an optical fiber disposed within a lumen of the inner member.

Continuing with reference to FIGS. 2 and 3A–3C, in an embodiment, catheter 100 includes an elongated catheter shaft 102 having a tubular inner member 104 and an outer member 106 disposed about the tubular inner member 104. An expandable member 108, for example an inflatable balloon 108, is coupled to a distal end 110 of the elongated catheter shaft 102. An adapter 112, such as a proximal triple port sidearm 112, is secured to the proximal ends of the inner and outer members 104, 106. Triple port sidearm 112 allows a port for guidewire 114 insertion, another port for passage of an inflating medium (not shown) for balloon 108 inflation, and a third port for insertion of the first and second fiber optics 30, 40 for performing LDV and thermal measurements.

The catheter shaft tubular inner member 104 generally extends from the proximal sidearm 112 to a catheter distal tip 110 while the outer member 106 extends from the proximal sidearm 112 to a balloon proximal seal area 116, where the outer member 106 is placed over and is fused to the proximal end of the balloon 108. Tubular inner member 104 may include at least one lumen 118, 118a–b longitudinally disposed therethrough that may be used by a guidewire 114 to position the catheter's distal tip 110, including the balloon 108, over a predetermined location within the body lumen that is to be treated. For a catheter configuration with an inner member 104 having multiple lumens 118a, 118b (as shown in FIG. 3), one lumen 118a is used as a guidewire lumen for guidewire 114 while the other lumen 118b may be used as a treatment lumen, for example as a radiation source lumen for passage of a radiation source 130 to a treatment site within a body lumen.

Balloon 108 may have a single lumen/single lobe arrangement, a multi-lumen/multi-lobe arrangement, or a combination thereof and may include tapered proximal and distal ends for enhanced treatment delivery, improved body lumen access, better balloon refolding, etc. The configuration of the inflatable balloon 108 generally depends on the type of application in which the balloon catheter 100 is to be used as well as other factors such as manufacturing preferences. For example, when used in the dilatation of a vessel, inflatable balloon 108 may generally have a single lumen/single lobe design. When used for radiation therapy or drug delivery applications, catheter 100 may typically include a balloon 108 having a multi-lumen/multi-lobe configuration for better centering or positioning within a body lumen.

Continuing with reference to 2 and 3A–3C, in one embodiment, first and second optical fibers 30, 40 are inserted into the intraluminal space or gap 120 between the outer member 106 and the inner member 104. In one configuration, first and second optical fibers 30, 40 may be movable, e.g. slideable within intraluminal space or gap 120. In another configuration (shown in FIG. 3A), first and second optical fibers 30, 40 may be fixedly coupled (i.e., secured) to the inner surface 106a of the shaft outer member 106 at a least one point along the outer member 106. This configuration will allow fibers 30, 40 to bend and "flex" easily as the catheter 100 tracks through tortuous anatomy. For optical transmission, the distal tips of fibers 30, 40 may be exposed through a notch 126 or an optical window present in the outer member 106 or it may be slightly extending past the distal tip 110 of catheter 100

In another embodiment (as shown in exemplary embodiment of FIG. 3B), optical fibers 30, 40 could be secured to the outer surface 104b of the shaft inner member 104 (to receive a guidewire 114 and radiation source 130) that extends to a distal tip 110 of the catheter 100. In this configuration, first and second optical fibers 30, 40 could be bonded to the inner member 104 at the distal balloon seal 122. This configuration would allow the tips of first and second optical fibers 30, 40 to be exposed for optical transmission at the distal tip 110 of catheter 100.

In an alternative embodiment (as shown in exemplary embodiment of FIG. 3C), optical fibers 30, 40 could be positioned within lumen 118b of the shaft inner member 104, while lumen 118a would be configured to receive a guidewire 114 and/or an inflation medium therethrough. In this configuration, optical fibers 30, 40 could be bonded to the inner member 104 or may be movable, e.g. slideable within lumen 118b.

The catheter shaft outer member 106 may be formed of suitable polymeric material such as high-density polyethylene (HDPE), a polyester such as Hytrel® (trademark of DuPont), poly-ether-ether-ketone (PEEK) or a variety other polymeric materials. The balloon 108 may be manufactured using balloon materials, such as Pebax™, nylon, polyethylene, polyurethane, or polyester. Materials for use in fabricating the balloon 108 of the present invention are selected by considering the properties and characteristics (e.g., softness, durability, low stiffness) required by angioplasty balloons, as well as considering properties necessary for successful balloon fabrication (e.g., balloon material compatible with other catheter materials and bonding process, material extruding well, etc.). The catheter shaft tubular inner member 104 may be formed of the same material as the outer member 106 or a lubricious material such as a fluoropolymer or a hydrophilic material, e.g. the ethylene ethyl acrylate co-polymer. The low friction surface of the inner wall of tubular inner member 104 facilitates the advancement of a guidewire 114 within the inner member lumen 118. The tubular inner member 104 may be a co-extruded member so that the exterior is compatible for fusion bonding to the balloon 108 and the interior has a lubricious surface. In an embodiment, catheter shaft tubular inner member 104 is manufactured as a co-extruded member having an inner portion manufactured from HDPE or similar material and an outer portion of Primacor or similar material.

It will be noted that catheter 100 may include any catheter type known in the art, for example an angioplasty catheter, a radiation delivery catheter, a stent deployment catheter, an imaging catheter, a drug delivery catheter, as well as any other type of medical catheters used in the field. Although catheter 100 is shown with an "over-the-wire" (OTW) catheter configuration, this invention is not limited to such catheter arrangements only. Those skilled in the art will recognize that this invention may also be practiced using a catheter with a "standard Rapid Exchange" (standard RX), "tip-RX", or any other catheter configuration known in the art. Furthermore, catheter 100 may have a single lumen inner member 104 (as shown in FIG. 3A), or alternatively, catheter 100 may have a multi-lumen inner member configuration (as shown in cross-sectional catheter views of FIGS. 3B–3C).

Continuing with reference to FIGS. 2 and 3A–3C, in an embodiment, first and second optical fibers 30, 40 are a single strand, single-mode glass optical fiber typically extending slightly beyond both the proximal and distal ends 128, 110 of catheter 100. A proximal extension length 34 of first optical fiber 30 allows for connection of the first optical fiber 30 to an LDV system 62 through a mechanical coupler 66 and an LDV optical fiber 68. A distal extension length of first optical fiber 30 allows for any necessary steps required to make the first optical fiber tip flush with, or extend slightly beyond the distal end 110 of catheter 100. Such steps can include, but are not limited to, cleaving the first optical fiber 30 at an angle, cutting the fiber 30 with a perpendicular face, or removing the fiber cladding as necessary to optimize light transmission/reception.

A proximal extension length 44 of second optical fiber 40 allows for connection of the first optical fiber 40 to an optical detector 62 through a mechanical coupler 66 and an optical fiber 70. A distal extension length of second optical fiber 40 has a Bragg diffraction grating 46 inscribed thereon to allow for temperature measurements.

The arrangement, sizes, material, etc. of first and second optical fibers 30, 40 used with therapeutic catheter 100 have been described. Furthermore, as stated above, it is within the scope of the present invention to have the therapeutic catheter 100 incorporate multiple optical fibers or a fiber optic bundle for each of the first and second optical fibers 30, 40. This arrangement may be advantageous for applications that would require performing thermal measurements and/or LDV measurements simultaneously at multiple sites in a vessel.

During its use in a medical procedure, the first fiber optic 30 of the therapeutic catheter 100 transmits and receives light for determining fluid flow velocities through a laser Doppler velocimetry (LDV) technique, while the second optical fiber 40, with its Bragg diffraction grating 46 written into it, measures local temperature.

As stated above, to perform LDV measurements, light is transmitted from a laser source 62A in the LDV system 62 through the optical fibers 30, 34, 68 and is scattered off of formed blood elements. The scattered light is collected by a detector 62B in the LDV system 62 as the light travels back through the optical fibers 30, 34, 68. The frequency content of the scattered light is indicative of the fluid velocity at the measurement site.

Measurements of local fluid temperature are obtained using optical fiber 40 having a Bragg diffraction grating 46 on its distal end. During manufacturing, strain-sensitive grating 46 is inscribed into the core of the optical fiber 40. As grating 46 of the fiber optic undergoes a temperature change due to the fluid temperature conducted along the fiber 40, the fringe spacing will correspondingly expand or contract as the fiber 40 is heated or cooled. The process results in a change in the index of refraction. As a result of this thermal induced strain in the grating, the light through the fiber 40 experiences this change in index of refraction, resulting in a change in the amount of light that is transmitted through the optical fiber 40. The therapeutic intravascular device 10 of this invention may be used to perform temperature measurements of the local fluid, e.g. blood, as well as of any body lumen structures, such as the arterial wall, etc.

Guidewire for Performing LDV and Thermal Measurements

Figure 4:
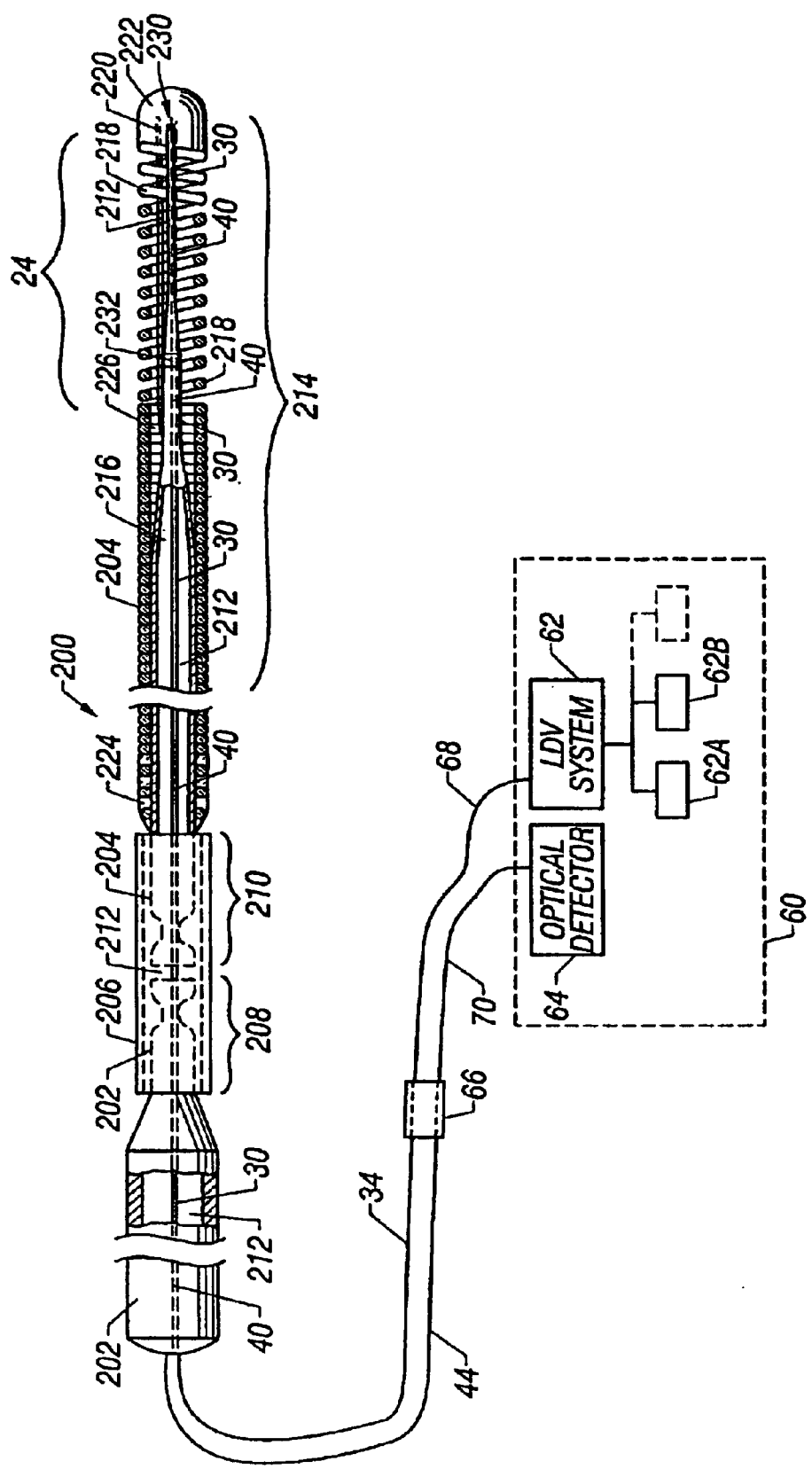
FIG. 4 illustrates generally an embodiment of a therapeutic guidewire for performing thermal and laser Doppler velocimetry measurements coupled to an LDV/thermal sensing apparatus and data processing system.

FIG. 4 illustrates generally an embodiment of a therapeutic guidewire 200 for performing thermal and laser Doppler velocimetry (LDV) measurements coupled to a data processing system 60. Guidewire 200 is adapted to be inserted into a patient's body lumen, such as an artery or vein. Any type and/or construction guidewire 200 used in the art may be employed within the scope of this invention. Depending on the type of application in which is to be used, the guidewire 200 is operatively coupled to a variety of intravascular/intraluminal treatment devices, including for example a balloon dilatation catheter for percutaneous transluminal coronary angioplasty (PTCA) and percutaneous transluminal angioplasty (PTA) procedures, an intravascular/intraluminal stent delivery system, a directional atherectomy device, a drug delivery device, a radiation treatment device, or any other intravascular/intraluminal treatment device used in the art.

Continuing with reference to FIG. 4, in one embodiment, the guidewire 200 includes an elongated core member that has a relatively high strength proximal core section 202 and a relatively short flexible distal core section 204. Depending on manufacturing preferences, type of application used, etc., guidewire 200 may include a connecting element 206 that joins a distal end 208 of the proximal core section 202 and a proximal end 210 of the distal core section 204. First and second optical fibers 30, 40 extend longitudinally through a lumen 212 present in and common to the proximal core section 202, the connecting element 206 and the distal core section 204. Alternatively, first and second optical fibers 30, 40 may extend longitudinally along the outside of the proximal core section 202, the connecting element 206 and the distal core section 204. First optical fiber 30 is for performing a laser Doppler velocity measurement of a fluid within the body lumen while the second optical fiber 40 is for performing a temperature measurement within the body lumen.

In one embodiment, proximal core section 202 and distal core section 204 are each formed from a hypotube made of stainless steel (SS) or of a pseudoelastic alloy material, such as Nickel-Titanium (Ni—Ti) alloy (e.g., Nitinol). The connecting element 206 is configured as a sleeve or hollow member that slightly overlaps the distal end 208 of proximal core section 202 and the proximal end 210 of distal core section 204. It should be noted that various configurations and/or shapes may be practiced within the scope of this invention.

Continuing with reference to FIG. 4, in the embodiment shown, the distal core section 204 has at least one tapered section 216 that becomes smaller in the distal direction. The tapered shape of distal core section 204 enhances the mechanical performance of the guidewire 200. Alternatively, the distal core section 204 may have a non-tapered shape, which generally simplifies the guidewire manufacturing process.

A flexible coil 218, generally having a helical configuration, is disposed about the distal core section 204.

Flexible coil 218 may be secured at its distal end to the distal end of a shaping ribbon 220 by a mass of bonding material, such as solder, which forms rounded tip 222 when it solidifies. The proximal end of the helical coil 218 may be secured to the distal core section 204 at a proximal location 224 and at intermediate location 226 by a suitable bonding material, e.g. solder. The proximal end of the shaping ribbon 220 may be secured to the distal core section 204 at the same intermediate location 226 by the bonding material, e.g. solder. The most distal section 228 of the helical coil 218 may be made of radiopaque metal, such as platinum or platinum-nickel alloys, to facilitate the fluoroscopic observation thereof while it is disposed within a patient's body.

In an embodiment, first and second optical fibers 30, 40 are exposed to a blood vessel of a patient at the distal tip 230 of the guidewire 200. Alternatively, guidewire 200 may have at least one opening 232, such as a window or a cutaway in its wall that allows first and second optical fibers 30, 40 to be exposed to a patient's vasculature and perform LDV and thermal measurements. Opening/window 232 may have any size and/or shape that is advantageous to first and second optical fibers 30, 40, guidewire 200 and/or guidewire manufacturing preferences. Alternatively, first and second optical fibers 30, 40 may be exposed to a patient's vasculature through guidewire coil 218.

With reference to FIG. 4, the most distal part 214 of the distal core section 204 may be manufactured to have various shapes and configurations, including for example be tapered and plunge-ground to a specific length, plunge-ground to a specific length only, or flattened into a rectangular cross-section.

The distal core section 204 can be made of a pseudoelastic alloy material, such as Nickel-Titanium (Ni—Ti) alloy (e.g., Nitinol). In one embodiment, the Ni—Ti alloy material consisting essentially of about 30 to about 52% titanium and the balance nickel and up to 10% of one or more other alloying elements. The other alloying elements may be selected from the group consisting of iron, cobalt, vanadium, platinum, palladium and copper. The alloy can contain up to about 10% copper and vanadium and up to 3% of the other alloying elements. In an embodiment, distal core section 204 has a length in a range of approximately 5–20 centimeters and an outer diameter of about 0.006–0.018 inches.

The elongated proximal core section 202 of the guidewire 200 is generally about 130 to about 300 centimeters in length with an outer diameter of about 0.006 to 0.018 inches (0.15–0.45 millimeters) for coronary use. Larger diameter guidewires, e.g. up to 0.035 inches (0.89 millimeters) or more may be employed in peripheral arteries and other body lumens. The lengths of the smaller diameter and tapered sections can range from about 1 to about 20 centimeters, depending upon the stiffness or flexibility desired in the final product. The helical coil 218 may be about 3 to about 45 centimeters in length, preferably about 5 to about 20 centimeters, has an outer diameter about the same size as the outer diameter of the elongated proximal core section 202, and is made from wire about 0.001 to about 0.003 inches (0.025–0.08 millimeters) in diameter, typically about 0.002 inches (0.05 millimeters). The shaping ribbon 220 and the flattened distal portion of distal core section 204 generally have rectangular-shaped transverse cross-sections which usually have dimensions of about 0.0005 to about 0.006 inches (0.013–0.152 millimeters), preferably about 0.001 by 0.003 inches (0.025–0.076 millimeters).

The high strength proximal core section 202 of guidewire 200 generally is significantly stronger, than the pseudoelastic distal portion. Suitable high strength materials include 304-stainless steel, which is a conventional material in guidewire construction. Other high strength materials include nickel-cobalt-molybdenum-chromium alloys such as commercially available MP35N alloy.

It will be noted that the above describes an exemplary guidewire configuration. Those skilled in the art will recognize that the therapeutic guidewire for performing LDV and thermal measurements of this invention may be practiced using other guidewire configurations and arrangements known in the art.

Continuing with reference to FIG. 4, in an embodiment, first and second optical fibers 30, 40 are a single strand, single-mode glass optical fiber typically extending slightly beyond both the proximal and distal ends of guidewire 200. A proximal extension length 34 of first optical fiber 30 allows for connection of the first optical fiber 30 to an LDV system 62 through a mechanical coupler 66 and an LDV optical fiber 68. A distal extension length of first optical fiber 30 allows for any necessary steps required to make the first optical fiber tip flush with, or extend slightly beyond the distal end 110 of catheter 100. Such steps can include, but are not limited to, cleaving the first optical fiber 30 at an angle, cutting the fiber 30 with a perpendicular face, or removing the fiber cladding as necessary to optimize light transmission/reception.

A proximal extension length 44 of second optical fiber 40 allows for connection of the first optical fiber 40 to an optical detector 62 through a mechanical coupler 66 and an optical fiber 70. A distal extension length of second optical fiber 40 has a Bragg diffraction grating 46 inscribed thereon to allow for temperature measurements.

The arrangement, sizes, material, etc. of first and second optical fibers 30, 40 used with guidewire 200 have been described. Furthermore, as stated above, it is within the scope of the present invention to have the guidewire 200 incorporate multiple optical fibers or a fiber optic bundle for each of the first and second optical fibers 30, 40. This arrangement may be advantageous for applications that would require performing thermal measurements and/or LDV measurements simultaneously at multiple sites in a vessel.

The therapeutic guidewire 200 having thermal sensing and LDV measurement capability is designed to function as a frontline guidewire by operatively coupling to various intravascular treatment devices, such as a catheter, a stent delivery device, etc. Therefore, its function is to cross a lesion and subsequently allow a catheter or stent delivery system to be passed over the guidewire to dilate the lesion. Guidewire 200 of this invention can also be used to interrogate the physiologic environment of the lesion before, during, or after therapy.

Method for Performing LDV and Thermal Measurements within Vasculature

FIGS. 1, 2 and 4 illustrate exemplary embodiments of a therapeutic intravascular device 10 for performing thermal and laser Doppler velocimetry measurements coupled to an LDV apparatus/thermal sensing and data processing system 60. The therapeutic medical device 10 may include any medical device, such as a catheter or a guidewire, used to treat intravascular conditions. With reference to FIGS. 1, 2 and 4, in an embodiment of a medical procedure, a distal portion of therapeutic intravascular device 10 (or catheter 100, guidewire 200) is inserted into a patient according to commonly known methods. Depending upon the type of medical procedure being performed, other medical devices may be coupled to device 10 (or catheter 100, guidewire 200). For example, if catheter 200 is to be used in a stenting procedure, an expandable metallic structure, such as stent (not shown), may be disposed, i.e., loaded, over the distal most tip of catheter body, typically over the balloon 108.

Hub or coupler 66 couples first optical fiber 30 (and its extension length 34) to an LDV system 62 via connecting optical fiber 68. The LDV system 62 may include various equipment known in the art of laser Doppler velocimetry measurement, for example a laser source 62A, a detector 62B, etc. Detector 62B may further include an amplifier (not shown), a signal processing unit (not shown), a computer system (not shown) which are to process the feedback signal received through the fiber optics 30, 34, 66. It is appreciated that any or all of laser source, amplifier, signal processing unit, computer system, etc. can be combined into an independent console unit.

Laser source 62A can be any continuous-wave signal or a high-repetition-rate pulsed laser. In one embodiment, laser source 62A is a modulated light diode or high-powered laser light source. The laser source is typically chosen based on the light wavelengths and light source power that facilitate the detection of the particular physical characteristic or variable. Specifically, because the light transmission window of blood is in the red to infrared (IR) range, a light wavelength in the range of 700 nm to 1500 nm may be used. It should be noted that longer wavelengths in the above stated range are desirable as they overcome some of the signal loss due to scattering in the blood. The shorter wavelengths are more energetic and therefore have the potential to cause tissue damage. In one embodiment, a wavelength of approximately 1300 nm may preferably be used.

The light output could be filtered if desired, as a homogenized illumination improves the signal-to-noise ratio. If the red or near-IR spectral range is used, laser diodes could be used as the excitation source to further improve the signal-to-noise ratio. Signal processing unit typically processes a signal from visual or light source data to electronic data or vice versa.

It is appreciated that a variety of components can be used to help generate, transmit and receive fiber optic signals. For example, a mono-chromator can be used to receive light signals transmitted back from the field of interest. The mono-chromator can also be fitted with a photodiode array detector, such as a 512 element intensified silicon photodiode array detector. Furthermore, a high-resolution filter grating can be installed in the mono-chromator in order to sharpen the features displayed in the spectral response for easier peak recognition and spectral analysis. A pulse generator can be used to time the detector response from the output pulse of the laser light signal.

In a typical embodiment of the present invention, a physician, e.g. cardiologist, usually first decides what portion of a vessel/treatment site is to be investigated, e.g., LDV and thermal measured. The physician will generally then insert the therapeutic medical device 10, 100, 200 with first and second optical fibers 30, 40 into the patient's vasculature and advances it to a specified location in the vasculature. Inserting and advancing medical device 10, 100, 200 is performed using methods well known in the art. Once the intravascular device 10, 100, 200 is in place, the LDV apparatus/thermal sensing and processing system 60 is operated to send and receive a plurality of light signals. The received reflected light signals are processed by the data processing system to provide information on a display such that the doctor can view this information and determine how to proceed.

Generally, to perform LDV measurements, light is transmitted from laser source 62A in the LDV system 62 through the optical fibers 30, 34, 68 and is scattered off of formed blood elements 52. The scattered light is collected by detector 62B in the LDV system 62 as the light travels back through the optical fibers 30, 34, 68. The frequency content of the scattered light is indicative of the fluid velocity at the measurement site.

In an alternative embodiment, the LDV system 62 uses two or more intersecting beams from a light source 62A, for example a laser source, and advanced optical data collection and processing equipment 62B to measure motion of individual minute particles as they pass through an imposed fringe pattern. The crossing of laser beams creates a "measurement volume" which consists of an interference fringe pattern of planar layers of high and low intensity light. Minute particles (e.g., 1 $\mu$m to 10 $\mu$m) present in the fluid backscatter the laser light with a frequency proportional to the flow velocity when passing through the measurement volume. The backscattered light is typically converted to an electrical signal with a photodetector or similar device. By using Fast Fourier Transform (FFT) techniques, the Doppler frequency is determined. The flow velocity is calculated with the known distance between the interference fringes and the measured frequency.

Measurements of local fluid temperature are obtained using optical fiber 40 having a Bragg diffraction grating 46 on its distal end. During manufacturing, strain-sensitive grating 46 is inscribed into the core of the optical fiber 40. As grating 46 of the fiber optic undergoes a temperature change due to the fluid temperature conducted along the fiber 40, the fringe spacing will correspondingly expand or contract as the fiber 40 is heated or cooled. The process results in a change in the index of refraction. As a result of this thermal induced strain in the grating, the light through the fiber 40 experiences this change in index of refraction, resulting in a change in the amount of light that is transmitted through the optical fiber 40. The therapeutic intravascular device 10 of this invention may be used to perform temperature measurements of the local fluid, e.g. blood, as well as of any body lumen structures, such as the arterial wall, etc.

Experimental Results

Catheter and guidewire based systems employing the features of this invention have been evaluated in various bench top configurations. For both LDV and thermal evaluations, these tests were conducted in anti-coagulated sheep blood in a benchtop pulsatile flow.

LDV Measurements

Figure 5:
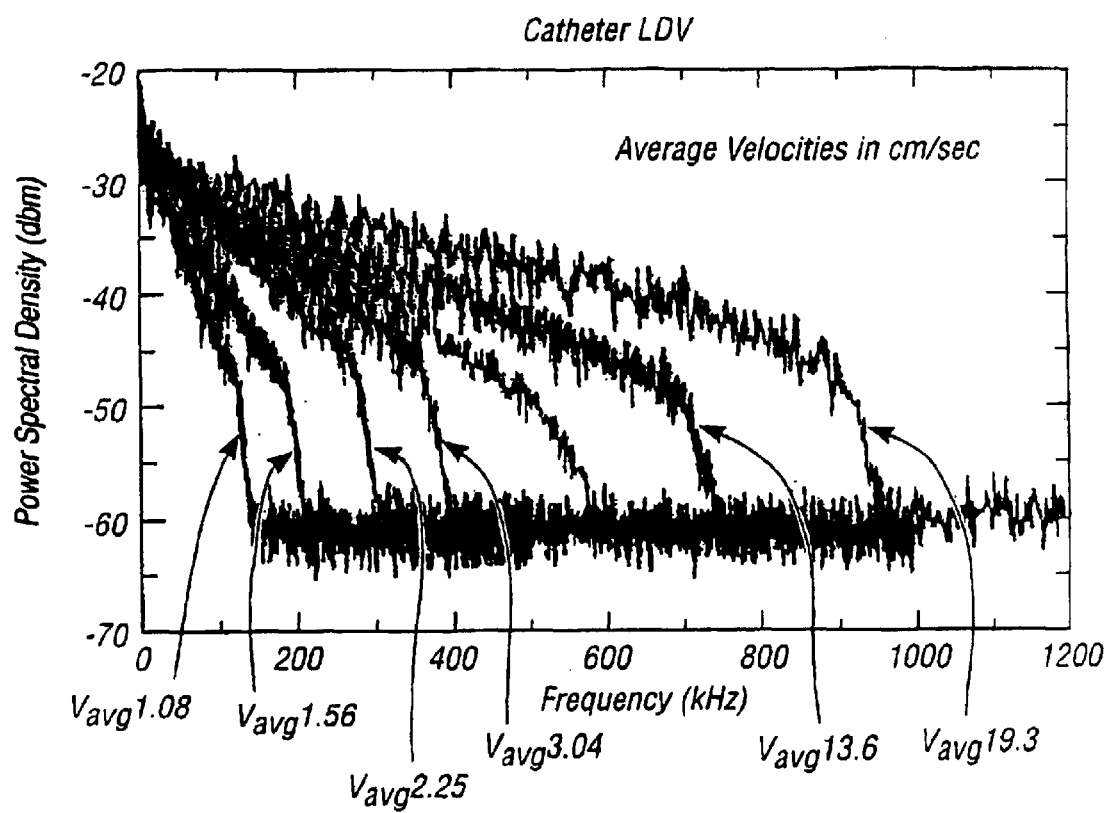
FIG. 5 shows Fast Fourier Transform (FFT) spectra obtained at peak output, averaged over multiple successive cycles, for a range of pump speeds conducted with a tested catheter prototype/LDV system.

FIG. 5 shows data obtained with a tested catheter prototype/LDV system that employed a 155 microns (micrometers, $\mu$m) glass fiber optic (having a 9.3 $\mu$m core) for the catheter prototype and a 250 $\mu$m glass (with a 9.3 $\mu$m core) LDV fiber optic. FIG. 5 shows Fast Fourier Transform (FFT) spectra obtained at peak output using the catheter system for a range of pump speeds (identified on the plots as $V_{avg}$) from 1.08–19.3 cm/s. The known pump flow speed is equivalent to the average flow velocity over the cross-sectional area of the tubing. The units on the axes are signal intensity (negative millidecibels, dB) versus frequency (kHz). The key feature of the spectra is the drop-off frequency at each flow speed, which corresponds to the most vertical region of each individual trace. For each peak output trace, the drop-off frequency corresponds to the average fluid flow velocity (as determined by the LDV system) at the measurement site. FIG. 5 demonstrates the sensitivity of the LDV/catheter system 100 to recording peak output flow signals over a range of pump speeds, and therefore over a range of fluid velocities.

Figure 6:
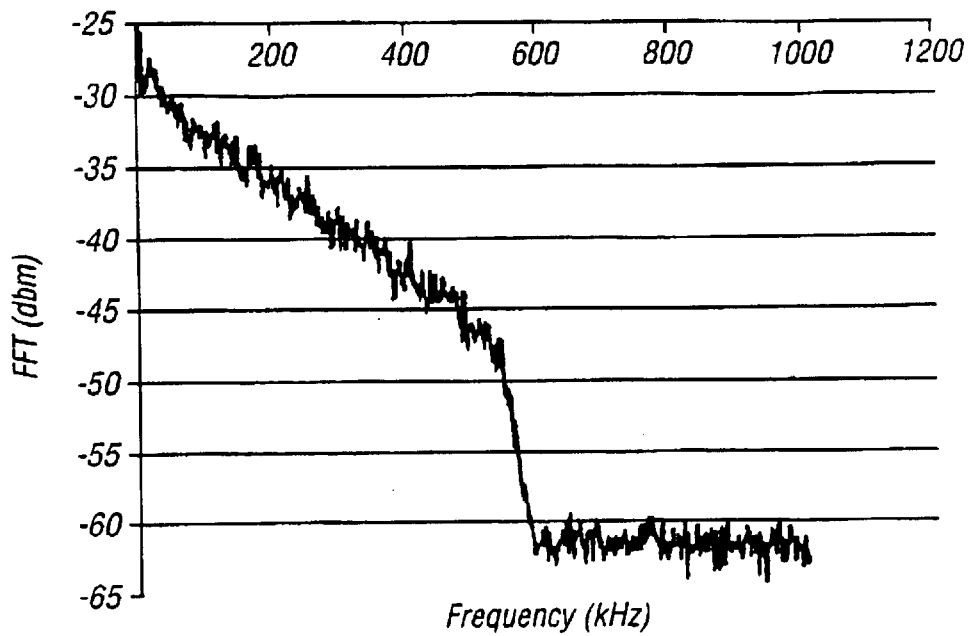
FIG. 6 shows FFT spectra obtained at peak output conducted with a tested guidewire prototype/LDV system.
Figure 7:
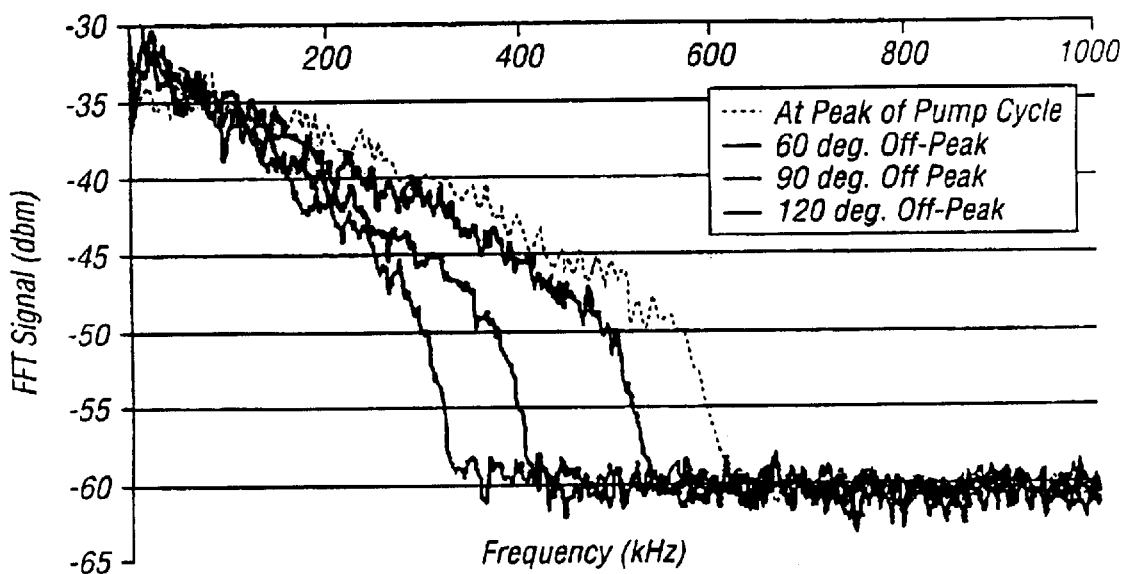
FIG. 7 shows FFT spectra at various pump cycle phases conducted with a tested guidewire prototype/LDV system.

FIGS. 6–7 relate to data obtained with a tested guidewire prototype/LDV system that employed a 155 microns (micrometers, $\mu$m) glass fiber optic (having a 9.3 $\mu$m core) for the catheter prototype and a 250 $\mu$m glass (with a 9.3 $\mu$m core) LDV fiber optic. FIG. 6 shows a Fast Fourier Transform (FFT) spectrum obtained at peak output, averaged over multiple successive cycles for the guidewire system. The units on the axes are intensity (negative mdB) versus frequency (kHz). This spectrum was obtained under peak output conditions, when the average velocity over the pump cycle was 18 cm/s. The key feature of the spectrum is the drop-off frequency, which corresponds to the steep region of the plot at approximately 560 kHz. At a given instant in the pump cycle, the drop-off frequency corresponded to the flow velocity. To determine particle velocity using the LDV technique, the raw Doppler signal is digitized and from the digitized signal FFT cross-spectra and power spectra are constructed, giving the Doppler frequency. The magnitude of the particle velocity is proportional to the Doppler frequency divided by the fringe spacing. FIG. 6 demonstrates the sensitivity of the LDV/guidewire system to recording peak output flow signals.

FIG. 7 shows FFT spectra obtained at various phases of pump cycle, the result of averaging over multiple successive cycles. The signal phases are as indicated in the legend (the signal labeled "at peak of pump cycle" is identical to that in FIG. 6). FIG. 7 demonstrates the temporal/phase sensitivity of the LDV/guidewire system throughout the pump cycle.

Thermal Measurements

Initial evaluations of a prototype for a catheter or guidewire based system 100, 200 having an optical fiber 40 for performing a temperature measurement have been conducted in a bench top flow system. The response of the optical fiber temperature sensor 40 was compared to that of a standard thermocouple, using water as the working fluid. Both the thermocouple and optical fiber temperature sensor 40 were bundled together in a section of copper tubing that was heated with a heating wire coil.

Figure 8A:
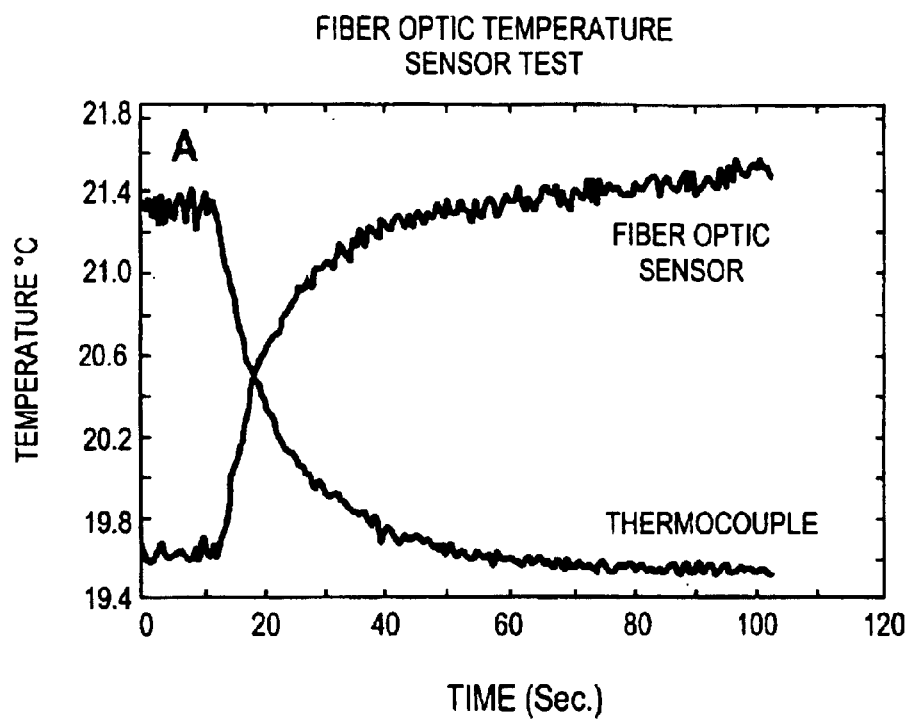
FIGS. 8A–8B show the responses of the optical fiber temperature sensor of this invention and a thermocouple following the sudden application/cessation of heat. Note: the two signals are almost identical although the polarity of the two signals is opposite due to an instrumental design choice for the optical detector electronics.
Figure 8B:
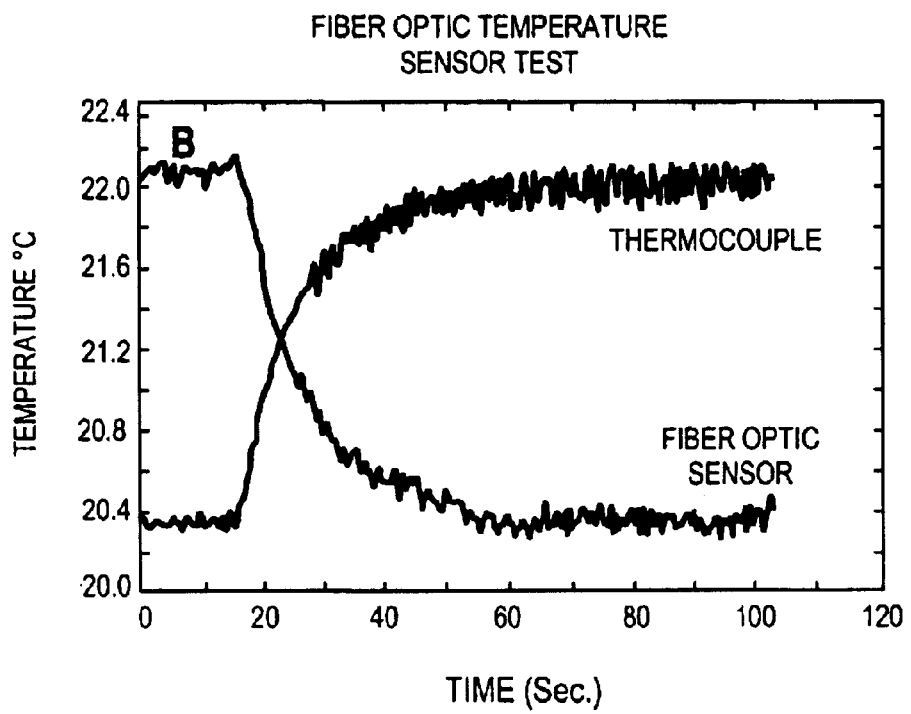

FIGS. 8A–8B show the responses of the optical fiber temperature sensor 40 and the thermocouple following the sudden application/cessation of heat. FIGS. 8A and 8B are the raw response data for the optical fiber temperature sensor 40 and thermocouple.

In FIG. 8A, the heating coil is suddenly turned off. As a result, the thermocouple records a drop in temperature from 21.4° C. to 19.5° C. (FIG. 8A). The optical fiber temperature sensor 40 measures the same magnitude temperature drop over the same period of time (the two signals are almost identical although the polarity of the two signals is opposite due to an instrumental design choice for the optical detector electronics). FIG. 8B shows the corresponding rise in temperature when the heating coil is turned on.

FIGS. 8A and 8B suggest that the resolution of the optical fiber temperature sensor 40 is on the order of 0.1° C. Both devices demonstrate the initial rapid and subsequent more gradual temperature variations that would be expected. Thus, the optical fiber temperature sensor 40 appears to record accurately the heating/cooling of the fluid without being subject to spurious noise detection.

Thus, the present invention describes an apparatus and method providing diagnostic and therapeutic capabilities through the use of an intravascular device having thermal and laser Doppler velocimetry (LDV) measurement capabilities. The LDV technique is known for high accuracy (up to 0.1%), a wide measuring range and for its high spatial and time resolution. The technique has been shown to have great potential for conducting in vivo blood flow measurements, even in challenging arterial anatomies. By integrating LDV technology and thermal sensing capability into a therapeutic guidewire system or a therapeutic catheter system, knowledge about a given lesion's in vivo biological environment can be obtained and utilized to make treatment decisions prior to, during, and after intervention. Such systems will provide clinicians with an enhanced set of tools with which to assess disease status in a given patient, a situation that will inevitably lead to improvements in both acute and chronic clinical outcomes.

We claim:

1. A therapeutic medical device for performing thermal and laser Doppler velocimetry measurements comprising:
    an elongated member;
    at least a first optical fiber longitudinally disposed through the elongated member to perform a laser Doppler velocimetry measurement of a fluid within the body lumen; and
    at least a second optical fiber longitudinally disposed through the elongated member to perform a temperature measurement within the body lumen.

2. The therapeutic medical device of claim 1 wherein distal ends of the first and second optical fibers are exposed within a vasculature of a patient at least at a one location along the therapeutic medical device.

3. The therapeutic medical device of claim 1 wherein at least one of the first and second optical fibers is fixedly coupled to the elongated member at least at a one location along the therapeutic medical device.

4. The therapeutic medical device of claim 1 wherein a proximal end of the first optical fiber is coupled to a laser Doppler velocimetry system.

5. The therapeutic medical device of claim 1 wherein a proximal end of the second optical fiber is coupled to an optical detector and a distal section of the second optical fiber has a Bragg diffraction grating formed thereon to perform the temperature measurement within the body lumen.

6. The therapeutic medical device of claim 1 wherein the elongated member has a treatment lumen selected from the group consisting of guidewire lumen, inflation lumen, radiation source lumen, drug delivery lumen, atherectomy device lumen and laparoscopy lumen.

7. The therapeutic medical device of claim 1 wherein the laser Doppler velocimetry measurement and the temperature measurement are performed simultaneously within the body lumen.

8. A catheter for performing thermal and laser Doppler velocimetry measurements, the catheter comprising:
    an elongated shaft comprising a tubular inner member having a first lumen therethrough and an outer member disposed about the tubular inner member; and
    first and second optical fibers longitudinally disposed through the first lumen of the tubular inner member,
    the first optical fiber to perform a laser Doppler velocimetry measurement of a fluid within a body lumen, the second optical fiber to perform a temperature measurement within the body lumen.

9. The catheter of claim 8 wherein distal ends of the first and second optical fibers are exposed within a vasculature of a patient at least at one location along the catheter.

10. The catheter of claim 8 wherein a proximal end of the first optical fiber is coupled to a laser Doppler velocimetry system.

11. The catheter of claim 8 wherein a proximal end of the second optical fiber is coupled to an optical detector and a distal section of the second optical fiber has a Bragg diffraction grating formed thereon.

12. The catheter of claim 8 wherein the tubular inner member has a second lumen longitudinally disposed therethrough.

13. The catheter of claim 12 wherein the second lumen is selected from the group consisting of guidewire lumen, inflation lumen, radiation source lumen, drug delivery lumen, atherectomy device lumen and laparoscopy lumen.

14. The catheter of claim 8 further comprises an expandable member coupled to a distal portion of the elongated tubular shaft.

15. The catheter of claim 13 wherein the expandable member is a balloon.

16. A guidewire for performing thermal and laser Doppler velocimetry measurements comprising:
- an elongated guidewire body comprising a distal core section axially coupled to a proximal core section, the elongated guidewire body having a lumen therethrough;
- an atraumatic distal tip formed at a distal end of the distal core section;
- at least a first optical fiber longitudinally disposed through the elongated guidewire body to perform a laser Doppler velocimetry measurement of a fluid within a body lumen; and
- at least a second optical fiber longitudinally disposed through the elongated guidewire body to perform a temperature measurement within the body lumen.

17. The guidewire of claim 16 wherein the guidewire is operatively coupled to a medical device to perform a therapeutic treatment.

18. The guidewire of claim 16 wherein a proximal end of the first optical fiber is coupled to a laser Doppler velocimetry system, a proximal end of the second optical fiber is coupled to an optical detector and a distal section of the second optical fiber has a Bragg diffraction grating formed thereon.

19. A guidewire for performing thermal and laser Doppler velocimetry measurements comprising:
- an elongated guidewire body comprising a distal core section axially coupled to a proximal core section, the elongated guidewire body having a lumen therethrough;
- an atraumatic distal tip formed at a distal end of the distal core section;
- at least a first optical fiber longitudinally disposed through the elongated guidewire body to perform a laser Doppler velocimetry measurement of a fluid within a body lumen; and
- at least a second optical fiber longitudinally disposed through the elongated guidewire body to perform a temperature measurement within the body lumen; and
- a connecting member coupling a distal end of the proximal core section to a proximal end of the distal core section.

20. A guidewire for performing thermal and laser Doppler velocimetry measurements comprising:
- an elongated guidewire body comprising a distal core section axially coupled to a proximal core section, the elongated guidewire body having a lumen therethrough;
- an atraumatic distal tip formed at a distal end of the distal core section;
- at least a first optical fiber longitudinally disposed through the elongated guidewire body to perform a laser Doppler velocimetry measurement of a fluid within a body lumen;
- at least a second optical fiber longitudinally disposed through the elongated guidewire body to perform a temperature measurement within the body lumen; and
- a flexible coil disposed about the distal core section of the elongated guidewire body, the flexible coil coupled to at least one point along the distal core section.

21. A guidewire for performing thermal and laser Doppler velocimetry measurements comprising:
- an elongated guidewire body comprising a distal core section axially coupled to a proximal core section, the elongated guidewire body having a lumen therethrough;
- an atraumatic distal tip formed at a distal end of the distal core section;
- at least a first optical fiber longitudinally disposed through the elongated guidewire body to perform a laser Doppler velocimetry measurement of a fluid within a body lumen;
- at least a second optical fiber longitudinally disposed through the elongated guidewire body to perform a temperature measurement within the body lumen; and
- a shaping ribbon coupled to the distal core section.

22. A system for performing thermal and laser Doppler velocimetry measurements, the system comprising:
- a laser Doppler velocimetry apparatus comprising a laser light source and an LDV detector coupled to a data processing system;
- an optical detector coupled to the data processing system; and
- a catheter coupled to the laser Doppler velocimetry apparatus and the optical detector, the catheter comprising an elongated shaft comprising a tubular inner member having a first lumen therethrough and an outer member disposed about the tubular inner member; the catheter further comprising first and second optical fibers longitudinally disposed through the first lumen of the tubular inner member, the first optical fiber to perform a laser Doppler velocimetry measurement of a fluid within a body lumen, the second optical fiber to perform a temperature measurement within the body lumen.

23. The system of claim 22 wherein the tubular inner member has a second lumen longitudinally disposed therethrough, the second lumen being selected from the group consisting of guidewire lumen, inflation lumen, radiation source lumen, drug delivery lumen, atherectomy device lumen and laparoscopy lumen.

24. A method for performing thermal and laser Doppler velocimetry measurements, the method comprising:
- inserting a therapeutic medical device into a vasculature of a patient, the therapeutic medical device comprising an elongated member having first and second optical fibers longitudinally disposed therethrough, the first optical fiber to perform a laser Doppler velocimetry measurement of a fluid within a body lumen, the second optical fiber to perform a temperature measurement within the body lumen;
- advancing the therapeutic medical device to a location in the vasculature;
- operating a data processing system coupled to the therapeutic medical device to transmit a plurality of light radiation signals to the location in the vasculature and a plurality of reflected light radiation signals to a detector in the data processing system; and processing the plurality of reflected light radiation signals to perform thermal and laser Doppler velocimetry measurements.

25. The method of claim 24 wherein the therapeutic medical device is a catheter.

26. The method of claim 24 wherein the therapeutic medical device is a guidewire operatively coupled to a catheter or a stent delivery system.

27. A catheter for performing thermal and laser Doppler velocimetry measurements, the catheter comprising:

an elongated shaft comprising a tubular inner member having first and second lumens therethrough and an outer member disposed about the tubular inner member, the second lumen being selected from the group consisting of guidewire lumen, inflation lumen, radiation source lumen, drug delivery lumen, atherectomy device lumen and laparoscopy lumen;

at least a first optical fiber longitudinally disposed through the first lumen of the tubular inner member, the first optical fiber having a proximal end coupled to a laser Doppler velocimetry apparatus and a distal end exposed to a vasculature of a patient; and at least a second optical fiber longitudinally disposed through the first lumen of the tubular inner member, the second optical fiber having a proximal end coupled to an optical detector and a distal end having a Bragg diffraction grating formed thereon.

* * * * *

UNITED STATES PATENT AND TRADEMARK OFFICE
CERTIFICATE OF CORRECTION

PATENT NO.    : 6,716,178 B1
DATED         : April 6, 2004
INVENTOR(S)   : Kilpatrick et al.

It is certified that error appears in the above-identified patent and that said Letters Patent is hereby corrected as shown below:

Title page,
Item [75], Inventors, "Deborah Kilpatrick", please delete "Mountain View" and insert -- Los Altos --; "Bridget A. Hurley", please delete "Mountain View" and insert -- San Francisco --; and "Jeffrey T. Ellis", please delete "Mountain View" and insert -- San Francisco --.

Signed and Sealed this

Twelfth Day of October, 2004

JON W. DUDAS
*Director of the United States Patent and Trademark Office*